(12) United States Patent
Yeo et al.

(10) Patent No.: US 8,606,353 B2
(45) Date of Patent: Dec. 10, 2013

(54) METHOD, MEDIUM, AND APPARATUS MEASURING BIOLOGICAL SIGNALS USING MULTI-ELECTRODE MODULE, WITH A LEAD SEARCH

(75) Inventors: Hyung-sok Yeo, Gyeonggi-do (KR); Jeong-whan Lee, Gyeonggi-do (KR); Mi-jeong Song, Gyeonggi-do (KR); Sung-Cheol Kim, Gyeonggi-do (KR); Jin-sang Hwang, Gyeonggi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1140 days.

(21) Appl. No.: 11/154,471

(22) Filed: Jun. 17, 2005

(65) Prior Publication Data
US 2006/0009691 A1    Jan. 12, 2006

(30) Foreign Application Priority Data

Jun. 17, 2004    (KR) .................. 10-2004-0045028

(51) Int. Cl.
*A61B 5/0404* (2006.01)
(52) U.S. Cl.
USPC ........................................... 600/521
(58) Field of Classification Search
USPC .................. 600/508, 509, 519, 521
See application file for complete search history.

(56) References Cited

U.S. PATENT DOCUMENTS

| | | | |
|---|---|---|---|
| 5,184,620 A | | 2/1993 | Cudahy et al. |
| 5,782,238 A | | 7/1998 | Beitler |
| 5,823,957 A | * | 10/1998 | Faupel et al. .......... 600/397 |
| 6,117,077 A | * | 9/2000 | Del Mar et al. .......... 600/301 |
| 6,453,186 B1 | | 9/2002 | Lovejoy et al. |
| 6,456,872 B1 | | 9/2002 | Faisandier |
| 2002/0038092 A1 | * | 3/2002 | Stanaland et al. .......... 600/509 |

FOREIGN PATENT DOCUMENTS

| | | | |
|---|---|---|---|
| JP | 62-183956 | 8/1987 | |
| JP | 2001-826450 | 10/2001 | |
| WO | 03/055387 | 7/2003 | |
| WO | WO 03/055387 | * 7/2003 | ........... A61B 5/0488 |

OTHER PUBLICATIONS

Korean Office Action dated Feb. 20, 2006 for Korean App. No. 10-2004-0045028.
Chinese Office Action issued Aug. 3, 2007 in corresponding Chinese Patent Application No. 200510087850.0.
Japanese Patent Office Action mailed Jul. 15, 2008 issued with respect to corresponding Japanese Patent Application 2005-178551.

* cited by examiner

*Primary Examiner* — Eric D. Bertram
(74) *Attorney, Agent, or Firm* — Staas & Halsey LLP

(57) ABSTRACT

A method, medium, and apparatus measuring biological signals using a multi-electrode module, with a lead search method. An apparatus for measuring biological signals by using a multi-electrode module, includes a multi-electrode module having a non-conductive patch and a sensor array including a ground electrode and a plurality of individual electrodes, an electrode selection unit selecting a plurality of electrode pairs including a reference electrode and a measurement electrode from the plurality of individual electrodes depending on a type of the biological signal to be measured, and a signal processing unit for obtaining the biological signals from the plurality of electrode pairs.

3 Claims, 20 Drawing Sheets

FIG. 10A
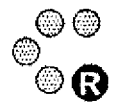
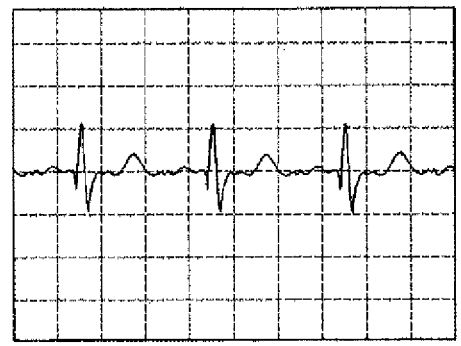
FIG. 10B
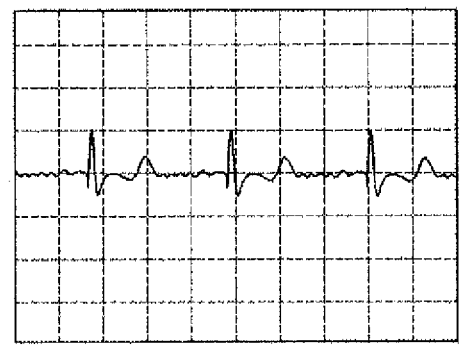
FIG. 10C

FIG. 10D
FIG. 10E
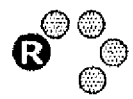
FIG. 10F
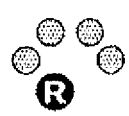
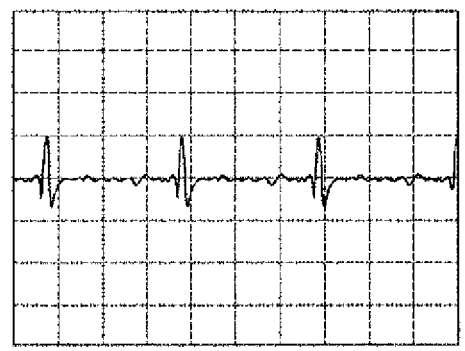

METHOD, MEDIUM, AND APPARATUS MEASURING BIOLOGICAL SIGNALS USING MULTI-ELECTRODE MODULE, WITH A LEAD SEARCH

CROSS-REFERENCE TO RELATED APPLICATIONS

This application claims the priority benefit of Korean Patent Application No. 10-2004-0045028, filed on Jun. 17, 2004, in the Korean Intellectual Property Office, the disclosure of which is incorporated herein in its entirety by reference.

BACKGROUND OF THE INVENTION

1. Field of the Invention

Embodiments of the present invention relate to the measurement of biological signals, and more particularly, to methods, media, and apparatuses measuring biological signals using a multi-electrode module, and a lead search method using the multi-electrode module, by which biological signals such as electrocardiograph (ECG) or heart rate (HR) can be measured regardless of the attachment location of the multi-electrode module and the arrangement directions of electrodes.

2. Description of the Related Art

Typically, in connection with medical appliances, electrodes are attached to particular positions of the human body to make a diagnosis. The electrodes are manufactured by interfacing different elements. A signal wire interconnects an analyzer instrument and metallic or conductive electrodes are attached to desired positions on a patient's skin. The combination of a wire and an electrode will be called a lead. Currents generated from the heart in the chest flow along the surface of the skin and produce a voltage difference between two electrodes attached to the skin. One of most available diagnosis tests using the electrodes attached to the human skin is the ECG. A general ECG measurement uses 12 lead positions to provide the most accurate signals for detecting variations of the ECG caused by ischemia. For the ECG measurement using the 12 lead positions, it is necessary to attach 10 electrodes to various positions on the patient's body and the limbs to analyze ECG data. 12 records on the ECG are read from first through ninth leads, with the tenth lead being used as a ground. Among the ten electrodes, six electrodes are applied to the patient's chest and remaining 4 electrodes are applied to the limbs according to predetermined anatomical landmarks. Usually, the electrodes applied to the chest are expressed as V1, V2, V3, V4, V5, and V6, respectively, and correspond to precordial leads. The electrodes applied to the limbs are expressed as LA, RA, LL, and RL (ground), respectively, and correspond to limb leads.

In order to obtain accurate and reproducible records, it is very important to accurately position the precordial leads. However, it is difficult to accurately arrange and attach these plurality of leads. Therefore, such a cumbersome operation consumes too much time and requisite knowledge, techniques, and efforts of a person attaching the electrodes. Often, the leads are not appropriately arranged and/or even attached in slightly lower or higher positions, thereby generating bad ECG data. On the other hand, a periodical ECG test is important to provide ECG profiles of the patient for early detection and diagnosis of cardiovascular diseases. For providing accurate ECG profiles, it is required that the electrodes be arranged in the same positions they were located in the previous test. The electrodes must also be securely fixed.

Unfortunately, according to the conventional ECG measurement technique of using 12 lead positions, the locations of attaching 6 precordial leads are nearly the same for every patient in spite that the locations of different patient's hearts being slightly different from each other. Therefore, it is difficult to make an accurate diagnosis. Furthermore, since 6 precordial leads have are often attached at slightly deviated locations every periodical ECG test, accuracy and reliability for persistent management of ECG data have been degraded.

To overcome such shortcomings, a multi-electrode module has been developed by integrating a plurality of electrodes into at least one module. However, it is also difficult to accurately identify the attachment location of the electrode module. Moreover, since the polarity of the active signal of the heart electricity may be changed depending on the arrangement directions of the electrodes, unskillful general users may feel inconvenienced.

SUMMARY OF THE INVENTION

Embodiments of the present invention provides a method, medium, and apparatus measuring biological signals using a multi-electrode module, where general users having no information on the attachment location of the electrode module or the arrangement directions of the electrodes can conveniently use the multi-electrode module, with the arrangement of the electrodes being simplified for measuring active signals of the heart electricity.

Also, embodiments of the present invention provide a lead search method using the multi-electrode module, by which a plurality of electrocardiograph signals can be reproducibly obtained from leads I, II and III of the Eindhoven's triangle with high speed.

To achieve the above and/or other aspects and advantages, embodiments of the present invention include a multi-electrode module for measuring biological signals, a nonconductive patch attachable to a human skin, and a sensor array arranged inside the nonconductive patch, the sensor array including a plurality of individual electrodes and a ground electrode, attachable to the human skin.

To achieve the above and/or other aspects and advantages, embodiments of the present invention include a multi-electrode module for measuring biological signals, including a nonconductive patch attachable to skin, and a sensor array arranged inside the nonconductive patch, the sensor array including a plurality of individual electrodes and a ground electrode, attachable to the skin, wherein an individual electrode of the plurality of individual electrodes placed at a center of remaining individual electrodes, of the plurality of individual electrodes, disposed in a substantially circular arc, is a reference electrode, and the remaining individual electrodes are sequentially selectable as a measurement electrode.

To achieve the above and/or other aspects and advantages, embodiments of the present invention include a multi-electrode module for measuring biological signals, including a nonconductive patch attachable to a skin, and a sensor array arranged inside the nonconductive patch, the sensor array including a plurality of individual electrodes and a ground electrode, attachable to the skin, wherein each of the individual electrodes, of the plurality of individual electrodes disposed in a substantially circular arc, are sequentially selectable as a reference electrode, and at least one of remaining individual electrodes, of the plurality of individual electrodes, excluding the selected reference electrode among the individual electrodes disposed in the substantially circular arc, are selectable as a measurement electrode.

To achieve the above and/or other aspects and advantages, embodiments of the present invention include a multi-electrode module for measuring biological signals, including a nonconductive patch attachable to skin, and a sensor array arranged inside the nonconductive patch, the sensor array including a plurality of individual electrodes and a ground electrode, attachable to the skin, wherein an individual electrode placed at a center of the individual electrodes, of the plurality of individual electrodes, disposed in a substantially circular arc is selectable as a reference electrode, and the individual electrodes disposed in the substantially circular arc are shorted to provide a single measurement electrode.

To achieve the above and/or other aspects and advantages, embodiments of the present invention include a method of measuring biological signals, including attaching a multi-electrode module to skin, the multi-electrode module including a nonconductive patch and a sensor array including a plurality of individual electrodes and a ground electrode, combining a plurality of electrode pairs, including a reference electrode and a measurement electrode, by selecting the reference electrode and the measurement electrode from the plurality of individual electrodes based on a type of biological signal measured, and obtaining the biological signals from the plurality of electrode pairs.

The method may further include searching for at least one lead, represented by at least one of the electrode pairs, to obtain electrocardiograph data, by analyzing the biological signals, as well as determining whether the ground electrode, the selected reference electrode, and the selected measurement electrode are electrically attached to the skin before obtaining the biological signals.

The searching for the at least one lead may include storing information of electrode pairs, including measurement and reference electrodes, and corresponding electrocardiograph data, comparing R-peaks of the stored electrocardiograph data to search for an electrode pair corresponding to electrocardiograph data having a highest positive R-peak, and selecting the electrode pair corresponding to the electrocardiograph data having the highest positive R-peak as a heart axis direction lead.

The searching for the at least one lead may also include storing information of electrode pairs, including measurement and reference electrodes, and corresponding electrocardiograph data, comparing R-peaks of the stored electrocardiograph data to search for a first electrode pair corresponding to electrocardiograph data having a highest positive R-peak, comparing R-peaks of the stored electrocardiograph data to search for a second electrode pair corresponding to electrocardiograph data having a lowest positive R-peak, selecting the first electrode pair as a lead II and setting a common electrode of the first and second electrode pairs as a negative electrode of the lead II and another electrode of the first electrode pair as a positive electrode of the lead II, selecting the second electrode pair as a lead I and setting the common electrode of the first and second electrode pairs as a negative electrode of the lead I and another electrode of the first electrode pair as a positive electrode of the lead I, and selecting a lead III by setting the positive electrode of the lead I as a negative electrode of the lead III and the positive electrode of the lead II as a positive electrode of the lead III.

The method may further include analyzing the biological signals to obtain a heart rate.

An individual electrode may be placed at a center of the plurality of individual electrodes, disposed in a substantially circular arc, and selected as a reference electrode, and the plurality of individual electrodes disposed in the substantially circular arc are sequentially selected as measurement electrodes. Further, each of the plurality of individual electrodes may be disposed in a substantially circular arc and sequentially selected as a reference electrode, and at least one of remaining individual electrodes, of the plurality of individual electrodes, excluding the reference electrode, may be selected as a measurement electrode. An individual electrode placed at a center of the plurality of individual electrodes, disposed in a substantially circular arc, may also be selected as a reference electrode, and the plurality of individual electrodes disposed in the substantially circular arc are shorted to provide a single measurement electrode.

To achieve the above and/or other aspects and advantages, embodiments of the present invention include an apparatus for measuring biological signals, including a multi-electrode module including a non-conductive patch and a sensor array including a ground electrode and a plurality of individual electrodes, an electrode selection unit to select a plurality of electrode pairs, including a reference electrode and a measurement electrode, from the plurality of individual electrodes based on a type of biological signal measured, and a signal processing unit to obtain the biological signals from the plurality of electrode pairs.

The electrode selection unit may include an operation unit to generate a predetermined control signal based on the type of the biological signal measured based on a user's input, a measurement signal selection unit to select an individual electrode placed at a center of the plurality of individual electrodes, disposed in a substantially circular arc, as the reference electrode for a reference signal, and sequentially selecting from the plurality of individual electrodes as the measurement electrode for a measurement signal, a measurement signal generating unit to select the individual electrode as the reference electrode for the reference signal and selecting the plurality of individual electrodes disposed on the substantially circular arc as the measurement electrode for the measurement signal, and a switch unit, in response to the control signal, to selectively connect the multi-electrode module to the measurement signal selection unit or the measurement signal generating unit.

The electrode selection unit may also includes an operation unit to generate a predetermined control signal based on the type of the biological signal measured based on a user's input, a reference/measurement signal selection unit to sequentially select each of the plurality of individual electrodes, disposed in a substantially circular arc, as the reference electrode for a reference signal, and selecting at least one of remaining plurality of individual electrodes disposed in the substantially circular arc as the measurement electrode for a measurement signal, a measurement signal generating unit to select an individual electrode placed at a center of the plurality of individual electrodes disposed in the substantially circular arc as the reference electrode for the reference signal and shorting output signals of the plurality of individual electrodes disposed in the substantially circular arc for a single measurement signal, and a switch unit, in response to the control signal, to selectively connect the multi-electrode module to the reference/measurement signal selection unit or the measurement signal generating unit. Here, the reference/measurement signal selection unit may add or short output signals of the remaining individual electrodes to provide the measurement signal.

To achieve the above and/or other aspects and advantages, embodiments of the present invention include an apparatus for measuring biological signals, including a multi-electrode module including a non-conductive patch and a sensor array including a ground electrode and a plurality of individual electrodes, attachable to skin, a measurement signal selection unit to select an individual electrode placed at a center of the plurality of individual electrodes, disposed in a substantially circular arc, as a reference electrode for a reference signal, and sequentially selecting the plurality of individual electrodes disposed in the substantially circular arc as a measurement electrode for a measurement signal, and a signal processing unit to process the measurement and reference signals by using a differential amplification to search for at least one lead.

To achieve the above and/or other aspects and advantages, embodiments of the present invention include an apparatus for measuring biological signals, including a multi-electrode module including a non-conductive patch and a sensor array including a ground electrode and a plurality of individual electrodes, attachable to skin, a reference/measurement signal selection unit to sequentially select each of the plurality of individual electrodes, disposed in a substantially circular arc, as a reference electrode for a reference signal, and at least one of remaining individual electrodes, of the plurality of individual electrodes excluding the reference electrode, as a measurement electrode for a measurement signal, and a signal processing unit to process the measurement and reference signals by using a differential amplification to search for at least one lead.

The reference/measurement signal selection unit may adds or shorts output signals of the remaining individual electrodes to provide the measurement signal.

The signal processing unit may further store information of electrode pairs, including measurement and reference electrodes, and corresponding electrocardiograph data, compare R-peaks of the stored electrocardiograph data to search for an electrode pair corresponding to electrocardiograph data having a highest positive R-peak, and select the electrode pair corresponding to the electrocardiograph data having the highest positive R-peak as a heart axis direction lead.

The signal processing unit may also further store information of electrode pairs, including measurement and reference electrodes, and corresponding electrocardiograph data, compare R-peaks of the stored electrocardiograph (data) to search for a first electrode pair corresponding to electrocardiograph data having a highest positive R-peak, compare R-peaks of the stored electrocardiograph data to search for a second electrode pair corresponding to electrocardiograph data having a lowest positive R-peak, select the first electrode pair as a lead II and sets a common electrode of the first and second electrode pairs as a negative electrode of the lead II and another electrode of the first electrode pair as a positive electrode of the lead II, select the second electrode pair as a lead I and sets the common electrode of the first and second electrode pairs as a negative electrode of the lead I and another electrode of the second electrode pair as a positive electrode of the lead I, and select a lead III by setting the positive electrode of the lead I as a negative electrode of the lead III and the positive electrode of the lead II as a positive electrode of the lead Ill.

Similarly, the signal processing unit may further store information of electrode pairs, including measurement and reference electrodes, and corresponding electrocardiograph data, compares R-peaks of the stored electrocardiograph data to search for an electrode pair corresponding to electrocardiograph data having a highest positive R-peak, and select the electrode pair corresponding to the electrocardiograph data having the highest positive R-peak as a heart axis direction lead.

In addition, the signal processing unit may further store information of electrode pairs, including measurement and reference electrodes, and corresponding electrocardiograph data, compare R-peaks of the stored electrocardiograph data to search for a first electrode pair corresponding to electrocardiograph data having a highest positive R-peak, compare R-peaks of the stored electrocardiograph data to search for a second electrode pair corresponding to electrocardiograph data having a lowest positive R-peak, select the first electrode pair as a lead II and setting a common electrode of the first and second electrode pairs as a negative electrode of the lead II and another electrode of the first electrode pair as a positive electrode of the lead II, select the second electrode pair as a lead I and setting the common electrode of the first and second electrode pairs as a negative electrode of the lead I and another electrode of the second electrode pair as a positive electrode of the lead I, and select a lead III by setting the positive electrode of the lead I as a negative electrode of the lead III and the positive electrode of the lead II as a positive electrode of the lead III.

To achieve the above and/or other aspects and advantages, embodiments of the present invention include an apparatus for measuring biological signals, including a multi-electrode module including a nonconductive patch and a sensor array including a ground electrode and a plurality of individual electrodes, attachable to skin, a measurement signal generating unit to select an individual electrode placed at a center of the plurality of individual electrodes, disposed in a substantially circular arc, as a reference electrode for a reference signal, and shorting output signals of the plurality of individual electrodes disposed in the substantially circular arc to provide a single measurement signal for a measurement signal, and a signal processing unit to process the measurement and reference signals by using a differential amplification to obtain a heart rate.

To achieve the above and/or other aspects and advantages, embodiments of the present invention include a lead search method for measuring biological signals, including attaching a multi-electrode module to skin, the multi-electrode module including a nonconductive patch and a sensor array including a plurality of individual electrodes and a ground electrode, storing information of electrode pairs, including a measurement electrode selected from the plurality of individual electrodes and a reference electrode selected from the plurality of individual electrodes, and corresponding electrocardiograph data, and comparing R-peaks of the stored electrocardiograph data to search for electrocardiograph leads.

An individual electrode, placed at a center of individual electrodes disposed in a substantially circular arc, may be selected as a reference electrode, and the individual electrodes disposed in the substantially circular arc are sequentially selected as measurement electrodes. Further, each of individual electrodes disposed in a substantially circular arc may be sequentially selected as reference electrodes, and at least one of remaining individual electrodes, excluding the reference electrode among the individual electrodes disposed in the substantially circular arc, may be selected as a measurement electrode.

The searching of the leads may also includes comparing R-peaks of the stored electrocardiograph data to search for an electrode pair corresponding to electrocardiograph data having a highest positive R-peak, and selecting the electrode pair corresponding to electrocardiograph data having a highest positive R-peak as a heart axis direction lead. The searching of the leads may also include comparing R-peaks of the stored electrocardiograph data to search for a first electrode pair corresponding to electrocardiograph data having a highest positive R-peak, comparing R-peaks of the stored electrocardiograph data to search for a second electrode pair corresponding to electrocardiograph data having a lowest positive R-peak, selecting the first electrode pair as a lead II and setting a common electrode of the first and second electrode pairs as a negative electrode of the lead II and another electrode of the first electrode pair as a positive electrode of the lead II, selecting the second electrode pair as a lead I and setting the common electrode of the first and second electrode pairs as a negative electrode of the lead I and another electrode of the second electrode pair as a positive electrode of the lead I, and selecting a lead III by setting the positive electrode of the lead I as a negative electrode of the lead III and the positive electrode of the lead II as a positive electrode of the lead III.

To achieve the above and/or other aspects and advantages, embodiments of the present invention include a medium including computer readable code implementing a method of measuring biological signals, the method including attaching a multi-electrode module to skin, the multi-electrode module including a nonconductive patch and a sensor array including a plurality of individual electrodes and a ground electrode, combining a plurality of electrode pairs, including a reference electrode and a measurement electrode, by selecting the reference electrode and the measurement electrode from the plurality of individual electrodes based on a type of measured biological signal, and obtaining the biological signals from the plurality of electrode pairs.

To achieve the above and/or other aspects and advantages, embodiments of the present invention include a medium including computer readable code implementing a lead search method for measuring biological signals, using a multi-electrode module including a nonconductive patch and a sensor array including a plurality of individual electrodes and a ground electrode, the method including storing information of electrode pairs, including a measurement electrode selected from the plurality of individual electrodes and a reference electrode selected from the plurality of individual electrodes, and corresponding electrocardiograph data, comparing R-peaks of the stored electrocardiograph data to search for an electrode pair corresponding to electrocardiograph data having a highest positive R-peak, and selecting the electrode pair corresponding to the electrocardiograph data having the highest positive R-peak as a heart axis direction lead.

To achieve the above and/or other aspects and advantages, embodiments of the present invention include a medium including computer readable code implementing a lead search method for measuring biological signals, using a multi-electrode module including a nonconductive patch and a sensor array including a plurality of individual electrodes and a ground electrode, the method including storing information of electrode pairs, including a measurement electrode selected from the plurality of individual electrodes and a reference electrode selected from the plurality of individual electrodes, and corresponding electrocardiograph data, comparing R-peaks of the stored electrocardiograph data to search for a first electrode pair corresponding to electrocardiograph data having a highest positive R-peak, comparing R-peaks of the stored electrocardiograph data to search for a second electrode pair corresponding to electrocardiograph data having a lowest positive R-peak, selecting the first electrode pair as a lead II and setting a common electrode of the first and second electrode pairs as a negative electrode of the lead II and another electrode of the first electrode pair as a positive electrode of the lead II, selecting the second electrode pair as a lead I and setting a common electrode of the first and second electrode pairs as a negative electrode of the lead I and another electrode of the second electrode pair as a positive electrode of the lead I, and selecting a lead III by setting the positive electrode of the lead I as a negative electrode of the lead III and the positive electrode of the lead II as a positive electrode of the lead III.

Additional aspects and/or advantages of the invention will be set forth in part in the description which follows and, in part, will be apparent from the description, or may be learned by practice of the invention.

BRIEF DESCRIPTION OF THE DRAWINGS

The above and other features and advantages of the present invention will become more apparent by describing in detail exemplary embodiments thereof with reference to the attached drawings in which:

FIGS. 10A through 10F illustrate waveform diagrams showing six ECG signals output from a differential amplifier unit when a multi-electrode module of FIG. 2 is adopted, according to an embodiment of the present invention;

DETAILED DESCRIPTION OF THE PREFERRED EMBODIMENTS

Figure 1:
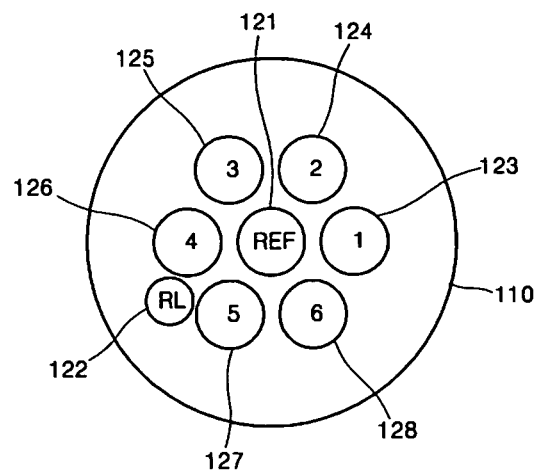
FIG. 1 illustrates a multi-electrode module for measuring biological signals, according to an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

FIG. 1 illustrates a multi-electrode module for measuring biological signals, according to an embodiment of the present invention. The multi-electrode module includes a nonconductive patch 110 attached to human skin, for example, a reference electrode 121, a ground electrode 122, and first through sixth individual electrodes 123 through 128. The reference electrode 121, the ground electrode 122, and the first through sixth individual electrodes 123 through 128 can be arranged inside the patch 110 and attached to the human skin, thereby making up a sensor array. In the sensor array, the reference electrode 121 is located at the center of the first through sixth individual electrodes 123 through 128, which are located in appropriate positions around the circular arc, covering 360°, for example.

According to this embodiment of the present invention, the first through sixth individual electrodes 123 through 128 can be sequentially selected as the measurement electrode, and a differential amplification of the output signal of each measurement electrode and the reference electrode 121 can be iterated six times for each measurement electrode. On the other hand, without adapting the reference electrode 121, two of the first through sixth individual electrodes 123 through 128 may be selected as the reference electrode and the measurement electrode, respectively.

Figure 2:
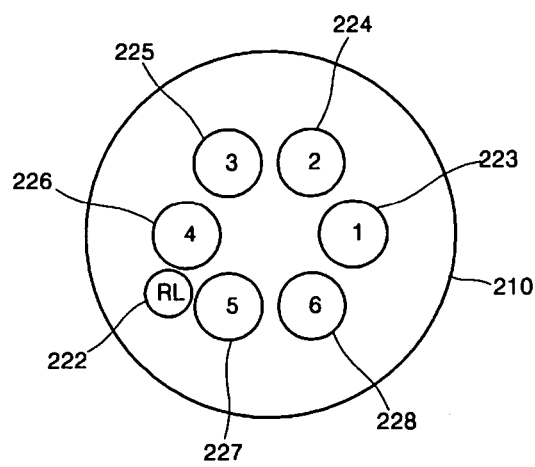
FIG. 2 illustrates a multi-electrode module for measuring biological signals, according to another embodiment of the present invention.

FIG. 2 illustrates a multi-electrode module for measuring biological signals, according to another embodiment of the present invention. The multi-electrode module includes a nonconductive patch 210 attached to the human skin, for example, a ground electrode 222, and first through sixth individual electrodes 223 through 228. The ground electrode 222, and the first through sixth individual electrodes 223 through 228 are arranged inside the patch 210 and attached to the human skin, thereby making up a sensor array. In the sensor array, the first through sixth individual electrodes 223 through 228 are located in appropriate positions around the circular arc, covering 360°, for example. A reference electrode may be variably selected from the individual electrodes. That is, one of the first through sixth individual electrodes 223 through 228 can be selected as the reference electrode, and the remaining individual electrodes can be selected as the measurement electrode. For example, the sixth electrode 228 may be selected as the reference electrode, and the remaining second through fifth electrodes 224 through 227 can be selected as the measurement electrode, such that signals output from each individual electrode are added. As another example, the sixth electrode 228 may be selected as the reference electrode, and the second through fifth electrodes 224 through 227 can be shorted to be used as the measurement electrode.

Figure 14:
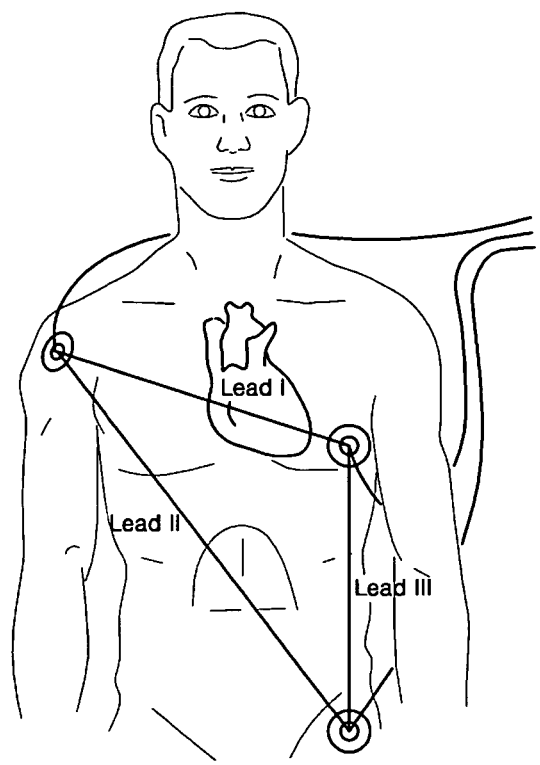
FIG. 14 illustrates a schematic diagram of leads I, II and III of the Eindhoven's triangle, according to an embodiment of the present invention.

Since the multi-electrode modules shown in FIGS. 1 and 2 are disposed on the patient's chest, to measure electrocardiograph (ECG) signals, they maintain a single fixed pattern with various kinds of geometries. All electrodes in the sensor array can be used to complete three leads I, II, and III of the Eindhoven's triangle for each patient. As discussed below, FIG. 14 illustrates theoretical leads I, II and III for an Eindhoven's triangle. Here, the theoretical illustration includes an ECG measurement using three lead positions based on the chest, performed in a left-to-right or right-to-left direction for a lead I, from the upper right chest to the left to the abdomen for a lead II, and from the upper left chest to the left to the abdomen for a lead III, thereby making up the Eindhoven's triangle.

Back to the multi-electrode module, each electrode in the sensor array can be connected to a biological signal analyzer (not shown in the drawing) through a wired communication such as an electrical lead wire. The communication method is not limited by such wired communication, but various communication methods may be utilized. For example, wireless communication using a Bluetooth module or optical communication may also be adopted. Each electrode is electrically contacted to the human skin, for example, to detect and transmit electrical signals generated from the patient. Preferably, each of the electrodes includes an electrode component, and a conductive polymeric adhesive material such as a hydro gel adhesive material electrically attached to the electrode component. Also, the shape of the electrode is not limited thereto, but various materials and structures may be utilized.

Figure 3:
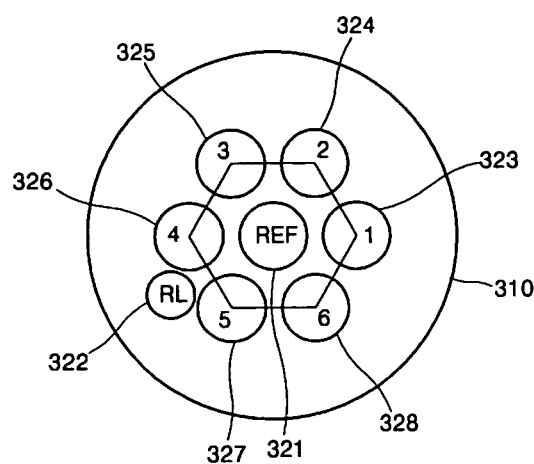
FIG. 3 illustrates a multi-electrode module for measuring biological signals, according to still another embodiment of the present invention.

FIG. 3 illustrates a multi-electrode module for measuring biological signals, according to still another embodiment of the present invention. The multi-electrode module includes a nonconductive patch 310 attached to the human skin, for example, a reference electrode 321, a ground electrode 322, and first through sixth individual electrodes 323 through 328. The reference electrode 321, the ground electrode 322, and the first through sixth individual electrodes 323 through 328 are arranged inside the patch 310 and attached to the human skin, thereby making up a sensor array. In the sensor array, the reference electrode 321 is located in the center of the first through sixth individual electrodes 323 through 328, which are located in appropriate positions around the circular arc, covering 360°, for example.

According to this embodiment, all of the first through sixth individual electrodes 323 through 328 can be shorted to be used as a measurement electrode, and a differential amplification of the output signal from the measurement electrode and the reference electrode 321 can be performed to measure a heart rate. Therefore, it is possible to obtain ECG signals having uniform polarity regardless of the attachment location of the electrode module and the arrangement directions of the electrodes, thereby effectively measuring a heart rate.

The multi-electrode modules shown in FIGS. 1 and 3 may be embodied as a single type by using the multi-electrode module shown in FIG. 1. In this case, it is necessary for a receiving side to appropriately process the signals output from each electrode arranged inside the patch 110, so that desired biological signals can be obtained to correspond to the arrangements of the multi-electrode modules of FIGS. 2 and 3.

Figure 4:
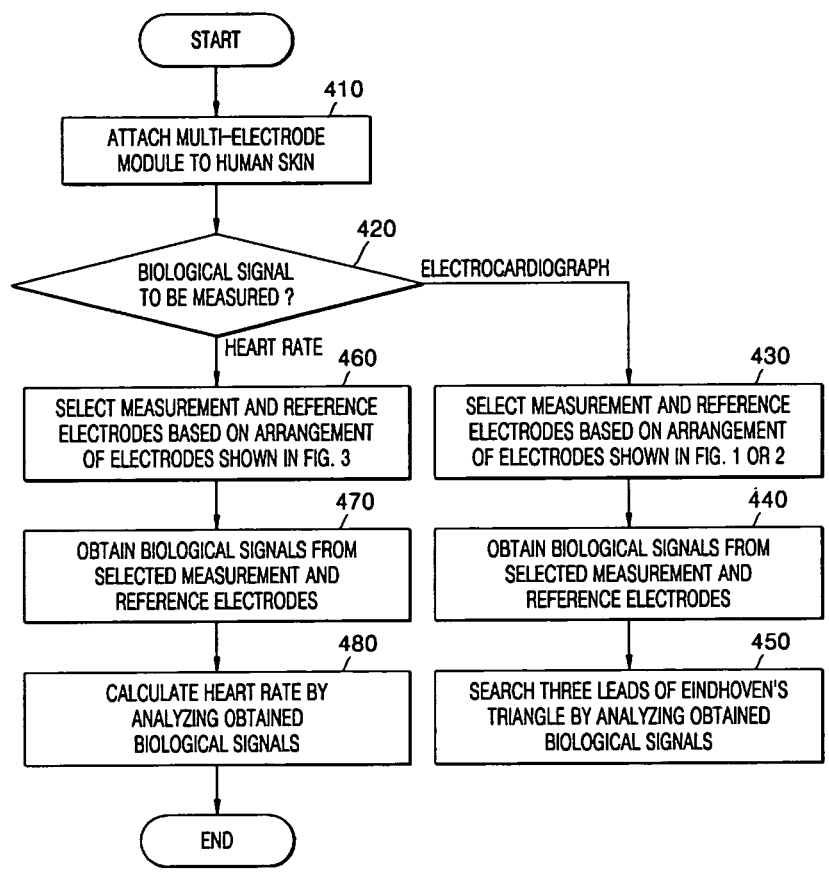
FIG. 4 illustrates a flowchart for measuring biological signals by using a multi-electrode module, according to an embodiment of the present invention.

FIG. 4 illustrates a flowchart for measuring biological signals by using a multi-electrode module, according to an embodiment of the present invention. The analysis of the biological signals, which will be described below, can be accomplished in a biological signal analyzer (not shown in the drawing).

In operation 410, the multi-electrode module can be attached to the human skin, for example. The multi-electrode module can include a nonconductive patch, and a sensor array, including a ground electrode and N individual electrodes arranged in a circular arc, where N is an integer equal to or greater than 2. In operation 420, whether a biological signal to be measured is a heart rate or an electrocardiograph is determined with reference to a user's input.

As a result of operation 420, if the electrocardiograph is measured, the measurement and reference electrodes are selected in operation 430 based on the arrangement of electrodes shown in FIG. 1 or 2. According to the arrangement shown in FIG. 1, an individual electrode positioned in the center is selected as the reference electrode, and the remaining (N-1) individual electrodes, excluding the reference electrode, are sequentially selected as the measurement electrode. According to the arrangement shown in FIG. 2, both the reference electrode and the measurement electrode are selected in a variable manner. If one of the (N-1) individual electrodes, excluding one positioned in the center, is selected as a reference electrode, the remaining (N-2) individual electrodes are selected as a measurement electrode. In the examples of FIGS. 1 and 2, N is set to 7.

In operation 440, (N-1) biological signals can be obtained by using the reference electrode and the measurement electrodes, selected in operation 430. In this case, (N-1) biological signals can also be used to determine whether there is an electrical miscontact in the leads. It is possible to determine the electrical miscontact of the leads if there is no input biological signal or if a period of the biological signals, filtered to eliminate power line noise and motion artifacts, is not within a predetermined normal range.

In operation 450, three leads I, II, and III of the Eindhoven's triangle are searched by analyzing the (N-1) biological signals obtained in operation 440. This will be described below.

As a result of operation 420, if a biological signal to be measured is the heart rate, the measurement and reference electrodes can be selected in operation 460 based on the arrangement of the electrodes shown in FIG. 3. According to the arrangement shown in FIG. 3, the individual electrode positioned in the center can be selected as a reference electrode, and remaining (N-1) individual electrodes, excluding the reference electrode, are shorted to be selected as a measurement electrode.

In operation 470, a single biological signal can be obtained by using the reference and measurement electrodes selected in operation 460. In this case, similarly to operation 440, the single biological signal can be used to determine whether there is an electrical miscontact of the leads. In operation 480, a heart rate can be calculated by analyzing the single biological signal obtained in operation 470.

Figure 5:
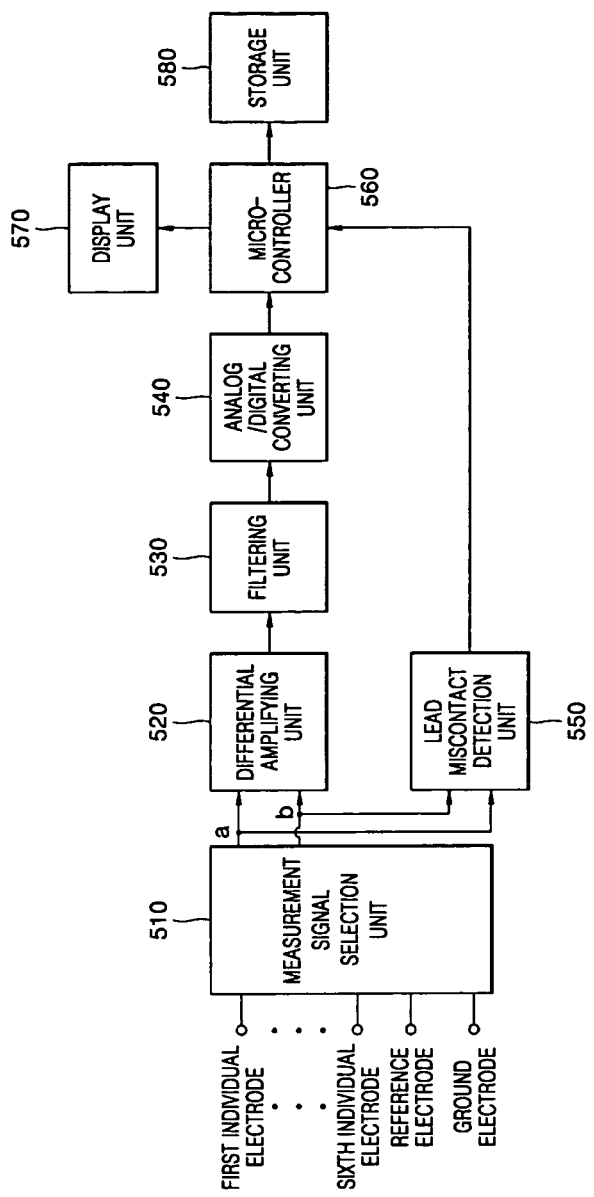
FIG. 5 illustrates a block diagram of an apparatus for measuring biological signals using a multi-electrode module, according to an embodiment of the present invention.

FIG. 5 illustrates an apparatus for measuring biological signals by using a multi-electrode module, according to an embodiment of the present invention. The apparatus includes a measurement signal selection unit 510, a differential amplifying unit 520, a filtering unit 530, an analog/digital (A/D) converting unit 540, a microcontroller 550, a lead miscontact detection unit 560, a display unit 570, and a storage unit 580. Preferably, the apparatus shown in FIG. 5 may use the multi-electrode module shown in FIG. 1, though embodiments of the present invention are not limited thereto. Now, operations of the apparatus for measuring biological signals according to an embodiment of the present invention will be described in association with the multi-electrode module of FIG. 1. For convenience in explanation, the number of the individual electrodes including the reference electrode has been set to 7, but is not limited thereto.

Referring to FIG. 5, the measurement signal selection unit 510 receives the measurement signals output from the first through sixth individual electrodes 123 through 128 and a reference signal output from the reference electrode 121. The measurement signal selection unit 510 provides a non-inverted input terminal a and an inverted input terminal b of a differential amplifying unit 520 with one of the measurement signals output from the first through sixth individual electrodes 123 through 128 and the reference signal output from the reference electrode 121. In this case, the measurement signals can be sequentially selected from the first through sixth electrodes 123 through 128. Furthermore, the ground electrode 122 can function as a right leg in an ECG tester using 12 lead positions.

The differential amplifying unit 520 performs a differential amplification for the measurement signals sequentially provided from the non-inverted input terminal a and the reference signal provided from the inverted input terminal b. The filtering unit 530 performs a filtering of the amplified signal output from the differential amplifying unit 520 to eliminate power line noise or motion artifacts. The A/D converting unit 540 converts the filtered signals output from the filtering unit 530 into digital signals and supplies the digital signals to the microcontroller 560.

The lead miscontact detection unit 550 detects electrical miscontact of the leads based on the measurement and reference signals output from the measurement signal selection unit 510, and outputs a signal representing a miscontact state or a normal state of the leads to the microcontroller 560. Herein, the miscontact of the leads means a state of no or bad electrical connection of the electrodes attached to the patient's skin for measuring biological signals. A filter may be installed on the front side of the lead miscontact detection unit 550 in order to increase reliability of detection of the lead miscontact.

The microcontroller 560 analyzes 6 digital signals output from the filtering unit 530 to obtain the leads I, II, III of the Eindhoven's triangle, assuming that the signal representing that the leads are at a normal state is input from the lead miscontact detection unit 550. If a signal representing a lead miscontact state is input from the lead miscontact detection unit 550, the microcontroller 560 does not enter into analysis of the 6 digital signals, but alarms the lead miscontact state via the display unit 570.

The display unit 570 may display the analysis result of the microcontroller 560 or the lead miscontact state through a character message or an alarm. The storage unit 580 stores the analysis result of the microcontroller 560.

Figure 6:
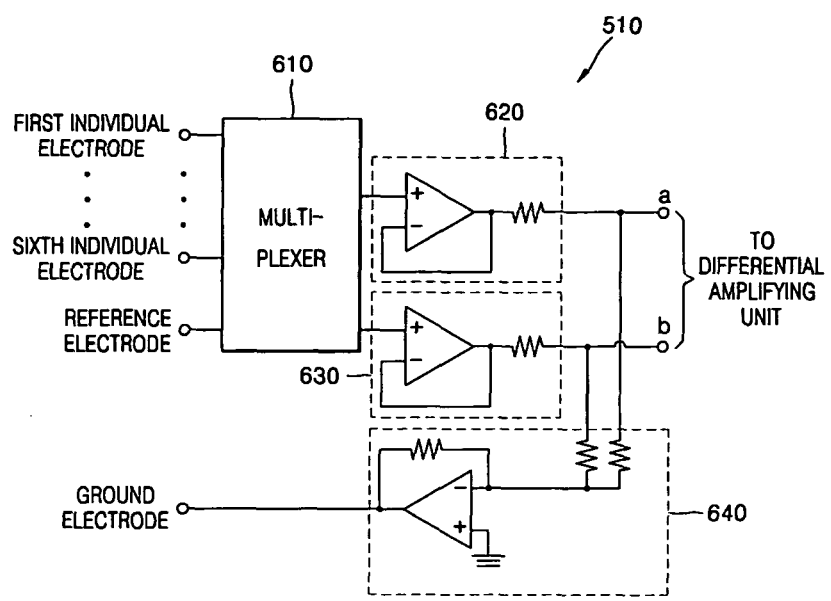
FIG. 6 illustrates a circuit diagram of a measurement signal selection unit, e.g., that of FIG. 5, according to an embodiment of the present invention.

FIG. 6 is a circuit diagram illustrating a measurement signal selection unit 510. The measurement signal selection unit includes a multiplexer 610, a first buffer 620, a second buffer 630, and an inverted amplifier 640.

The multiplexer 610 selects one of the measurement signals output from the first through sixth individual electrodes 123 through 128 in a sequential manner, and transmits the selected measurement signals to the first buffer 620. Also, the multiplexer 610 delivers the reference signal output from the reference electrode 121 to the second buffer 630. Furthermore, the multiplexer 610 may select two of the signals transmitted from the first through sixth individual electrodes 123 through 128 as a measurement signal and a reference signal, respectively, and transmit the selected measurement and reference signal to the first and second buffers 620 and 630, respectively.

The first and second buffers 620 and 630 buffer the measurement and reference signals and output the buffered signals to the non-inverted input terminal a and the inverted input terminal b of the differential amplifying unit 520, respectively. The inverted amplifier 640 amplifies the signals delivered to the non-inverted input terminal a and the inverted input terminal b of the differential amplifying unit 520 to eliminate power line noise and stabilize the voltage of the ground electrode 122.

Figure 7A:
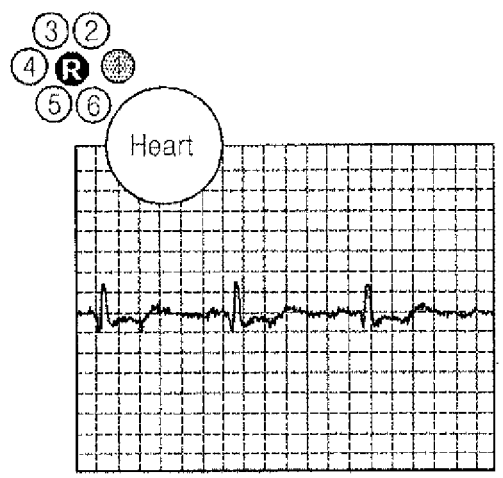
FIGS. 7A through 7F illustrate waveform diagrams showing six ECG signals output from a differential amplifier unit when a multi-electrode module of FIG. 1 is adopted, according to an embodiment of the present invention.
Figure 7B:
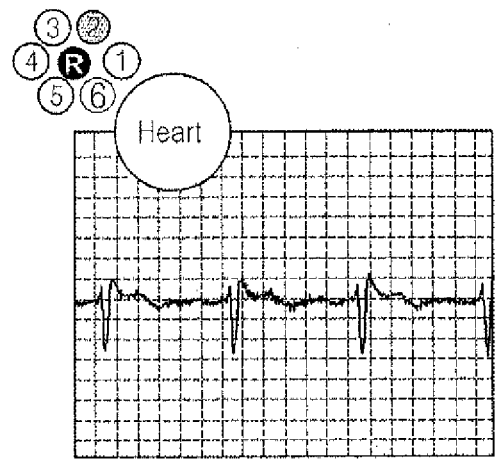
Figure 7C:
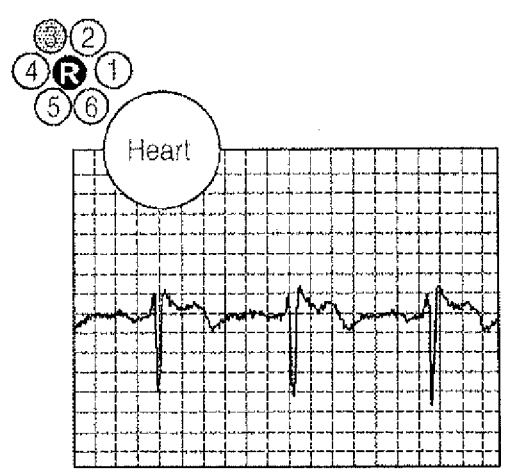
Figure 7D:
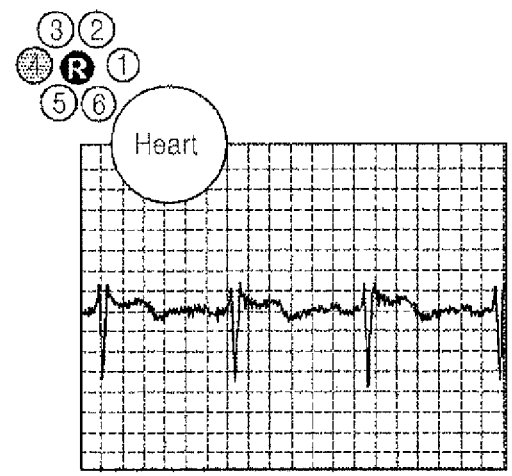
Figure 7E:
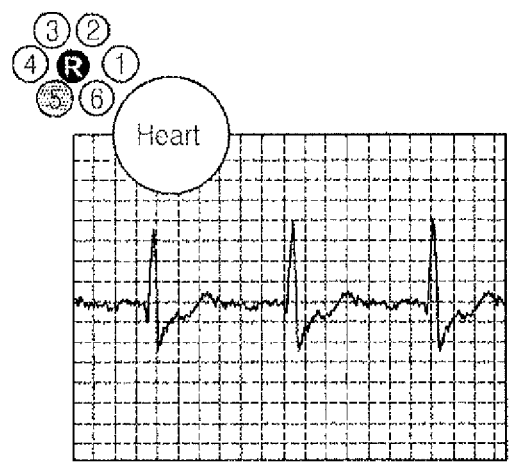
Figure 7F:
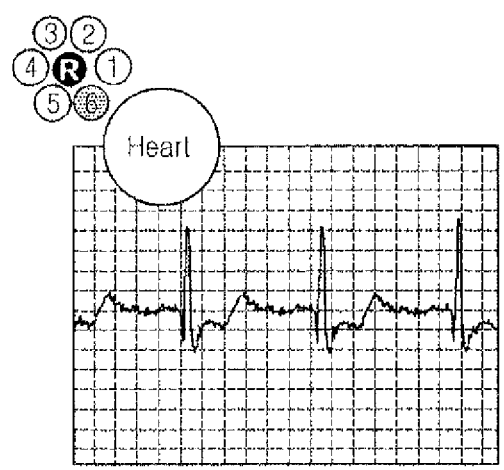

FIGS. 7A and 7F illustrate waveform diagrams showing six ECG signals output from a differential amplifying unit 520 of FIG. 5, for example, when a multi-electrode module of FIG. 1 is adopted, wherein a horizontal axis refers to time (0.2 s/Div.), and a vertical axis refers to voltage (0.1V/Div.).

More specifically, FIG. 7A shows an output signal of a differential amplifying unit 520 when a reference signal of a reference electrode 121 and a measurement signal of a first individual electrode 123 are input. FIG. 7B shows an output signal of a differential amplifying unit 520 when a reference signal of a reference electrode 121 and a measurement signal of a second individual electrode 124 are input. FIG. 7C shows an output signal of a differential amplifying unit 520 when a reference signal of a reference electrode 121 and a measurement signal of a third individual electrode 125 are input. FIG. 7D shows an output signal of a differential amplifying unit 520 when a reference signal of a reference electrode 121 and a measurement signal of a fourth individual electrode 126 are input. FIG. 7E shows an output signal of a differential amplifying unit 520 when a reference signal of a reference electrode 121 and a measurement signal of a fifth individual electrode 127 are input. FIG. 7F shows an output signal of a differential amplifying unit 520 when a reference signal of a reference electrode 121 and a measurement signal of a sixth individual electrode 128 are input.

Figure 8:
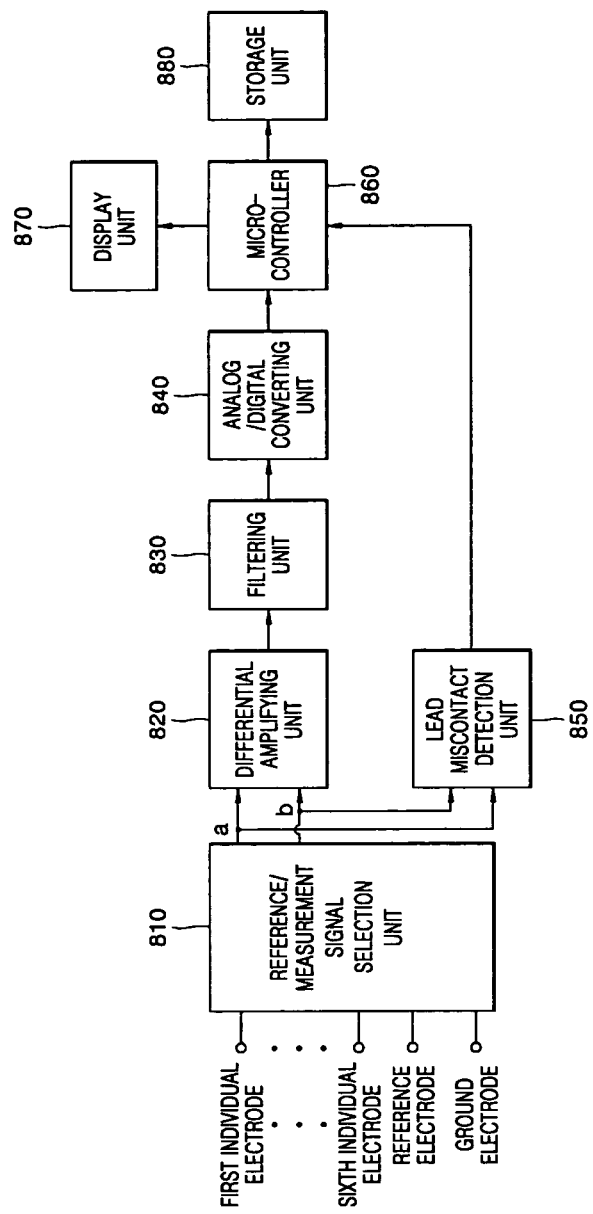
FIG. 8 illustrates a block diagram of an apparatus for measuring biological signals using a multi-electrode module, according to another embodiment of the present invention.

FIG. 8 illustrates a block diagram for an apparatus for measuring biological signals using a multi-electrode module, according to another embodiment of the present invention. The apparatus includes a reference/measurement signal selection unit 810, a differential amplifying unit 820, a filtering unit 830, an A/D converting unit 840, a lead miscontact detection unit 850, a microcontroller 860, a display unit 870, and a storage unit 880. Preferably, the apparatus shown in FIG. 8 uses the multi-electrode module shown in FIG. 2, and has a similar construction to that shown in FIG. 5, according to an embodiment of the present invention, except for the reference/measurement signal selection unit 810, though embodiments of the present invention are not limited thereto. Now, operations of the apparatus for measuring biological signals according to a second embodiment of the present invention will be described in association with the multi-electrode module of FIG. 2, and detailed descriptions will not be repeated for parts similar to those shown in FIG. 5. For simplicity in explanation, the number of the individual electrodes, including the reference electrode, is set to 6, but not limited by this number.

Referring to FIG. 8, the reference/measurement signal selection unit 810 may receive signals from the first through sixth individual electrodes 223 through 228. The reference/measurement signal selection unit 810 can buffer one of the signals transmitted from the first through sixth individual electrodes 223 through 228 and then select the buffered signal as a reference signal, according to control by the microcontroller 860. In addition, the reference/measurement signal selection unit 810 can buffer the remaining signals transmitted from the first through sixth individual electrodes 223 through 228, and then sum up, or short, the buffered remaining signals for use as the measurement signal. The selected measurement signal and the reference signal are then provided to the non-inverted input terminal a and the inverted input terminal b of the differential amplifier unit 820, respectively. In this case, the ground electrode 222 can function as a right leg in an ECG tester using 12 lead positions. For example, the output signal of the first individual electrode 223 can be used as a reference signal, and the sum of the output signals of the second through sixth individual electrodes 224 through 228 can be used as a measurement signal. As another example, the output signal of the first individual electrode 223 can be used as a reference signal, and the output signals of the second through sixth individual electrodes 224 through 228 can be shorted and used as the measurement signal.

Figure 9:
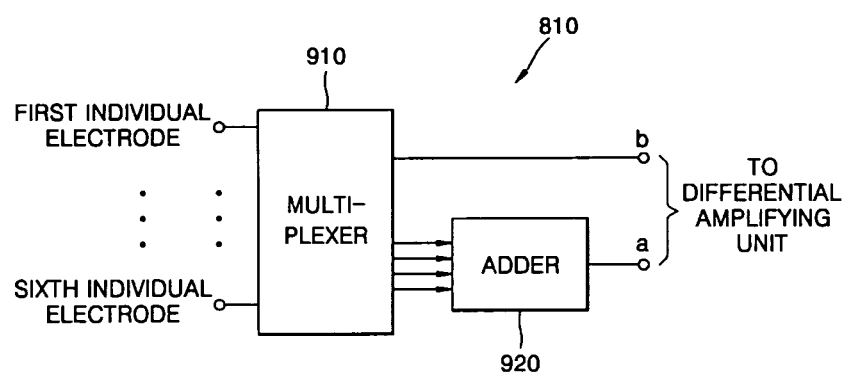
FIG. 9 illustrates a circuit diagram of a reference/measurement signal selection unit, e.g., that of FIG. 8, according to an embodiment of the present invention.

FIG. 9 illustrates a circuit diagram for a reference/measurement signal selection unit 810 of FIG. 8, for example. The reference/measurement signal selection unit 810 includes a multiplexer 910 and an adder 920. Though not shown in the drawing, a buffer may be included within the output terminal of the multiplexer 910.

The multiplexer 910 selects one of the first through sixth individual electrodes 223 through 228 as a reference electrode, and delivers the reference signal transmitted from the selected reference electrode to the inverted input terminal b of the differential amplifying unit 820.

The adder 920 adds the output signals of the remaining 5 individual electrodes except, for the one selected by the multiplexer 910 as the reference electrode, and outputs the sum to the non-inverted input terminal a of the differential amplifying unit 820.

FIGS. 10A through 10F illustrate waveform diagrams of six ECG signals output from a differential amplifying unit 820 of FIG. 8 when a multi-electrode module of FIG. 2 is adopted, wherein a horizontal axis refers to time (0.2 s/Div.), and a vertical axis refers to voltage (0.1V/Div.). In this case, one individual electrode is selected as a reference electrode, and four individual electrodes around the circular arc are selected as measurement electrodes.

More specifically, FIG. 10A shows an output signal of a differential amplifying unit 820 when an output signal of the sixth individual electrode 228 is selected as a reference signal and the sum of the output signals of the second through fifth individual electrodes 224 through 227 is selected as a measurement signal. FIG. 10B shows an output signal of a differential amplifying unit 820 when an output signal of the first individual electrode 223 is selected as a reference signal and the sum of the output signals of the third through sixth individual electrodes 225 through 228 is selected as a measurement signal. FIG. 10C shows an output signal of a differential amplifying unit 820 when an output signal of the second individual electrode 224 is selected as a reference signal and the sum of the output signals of the first, fourth, fifth and sixth individual electrodes 223, 226, 227 and 228 is selected as a measurement signal. FIG. 10D shows an output signal of a differential amplifying unit 820 when an output signal of the third individual electrode 225 is selected as a reference signal and the sum of the output signals of the first, second, fifth, and sixth individual electrodes 223, 224, 227 and 228 is selected as a measurement signal. FIG. 10E shows an output signal of a differential amplifying unit 820 when an output signal of the fourth individual electrode 224 is selected as a reference signal and the sum of the output signals of the first, second, third and sixth individual electrodes 223, 224, 225 and 228 is selected a measurement signal. FIG. 10F shows an output signal of a differential amplifying unit 820 when an output signal of the fifth individual electrode 227 is selected as a reference signal and the sum of the output signals of the first through fourth individual electrodes 223 through 226 is selected as a measurement signal.

Figure 11:
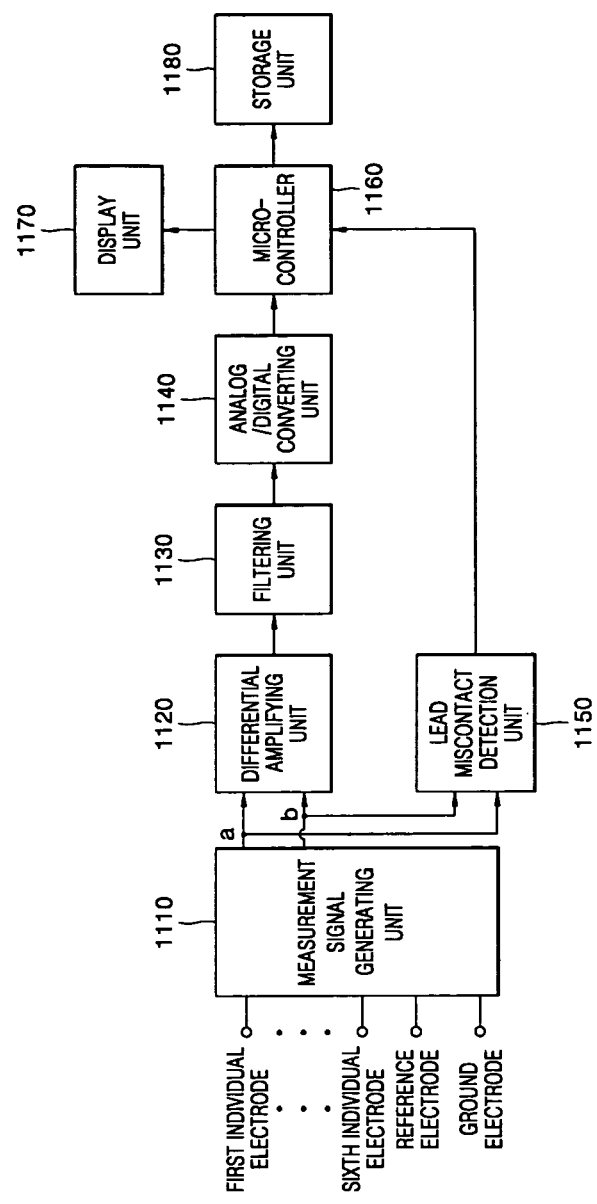
FIG. 11 illustrates a block diagram of an apparatus for measuring biological signals by using a multi-electrode module, according to still another embodiment of the present invention.

FIG. 11 illustrates a block diagram of an apparatus for measuring biological signals by using a multi-electrode module, according to another embodiment of the present invention. The apparatus includes a measurement signal generating unit 1110, a differential amplifying unit 1120, a filtering unit 1130, an A/D converter unit 1140, a microcontroller 1160, a lead miscontact detection unit 1150, a display unit 1170, and a storage unit 1180. Preferably, the apparatus shown in FIG. 11 uses the multi-electrode module shown in FIG. 3, and has a similar construction to that shown in FIG. 5 according to an embodiment of the present invention, except for the measurement signal generating unit 1110, though embodiments of the present invention are not limited thereto. Now, operations of the apparatus for measuring biological signals will be described in association with the multi-electrode module of FIG. 3, and detailed descriptions will not be repeated for parts similar to those shown in FIG. 5. For simplicity in explanation, the number of the individual electrodes including the reference electrode is set to 7, but is not limited by this number.

Referring to FIG. 11, the measurement signal generating unit 1110 receives signals from the first through sixth individual electrodes 323 through 328. The measurement signal generating unit 1110 shorts the output signals of the first through sixth individual electrodes 323 through 328 to generate a measurement signal, and selects the output signal of the reference electrode 321 as a reference signal. The measurement and reference signals are applied to the non-inverted input terminal a and the inverted input terminal b of the differential amplifying unit 1120, respectively. In this case, the ground electrode 322 can function as a right leg in an ECG tester using 12 lead positions.

Figure 12:
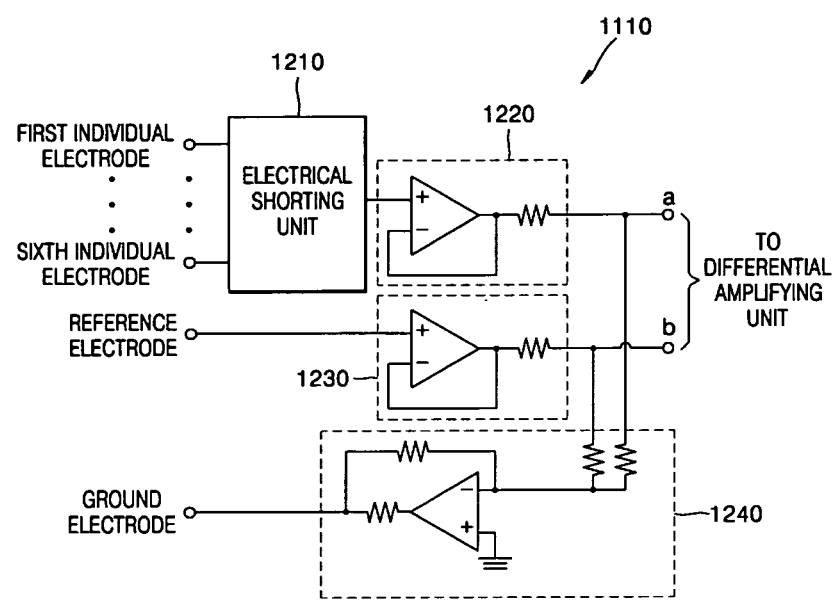
FIG. 12 illustrates a circuit diagram of a measurement signal generating unit, e.g., that of FIG. 11, according to an embodiment of the present invention.

FIG. 12 illustrates a circuit diagram of a measurement signal generating unit 1110 of FIG. 11, for example. The measurement signal generating unit 1110 includes an electrical shorting unit 1210, first and second buffers 1220 and 1230, and an inverted amplifier 1240. In FIG. 12, since the first and second buffers 1220 and 1230 and the inverted amplifier 1240 are similar to those shown in FIG. 6, their detailed descriptions will not be repeated.

In FIG. 12, the electrical shorting unit 1210 shorts the output signals of the first through sixth individual electrodes 323 through 328 to generate a measurement signal, and then transmits the measurement signal to the non-inverted input terminal a of the differential amplifying unit 1120 via the first buffer 1220.

FIGS. 13A through 13D illustrate waveform diagrams for output signals of a differential amplifying unit 1120 of FIG. 11.

Figure 13A:
FIGS. 13A through 13D illustrate waveform diagrams showing a single electrocardiograph signal output from a differential amplifier unit when a multi-electrode module of FIG. 3 is adopted, according to an embodiment of the present invention.
Figure 13B:
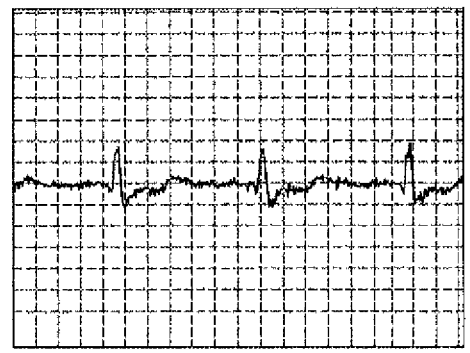
Figure 13C:
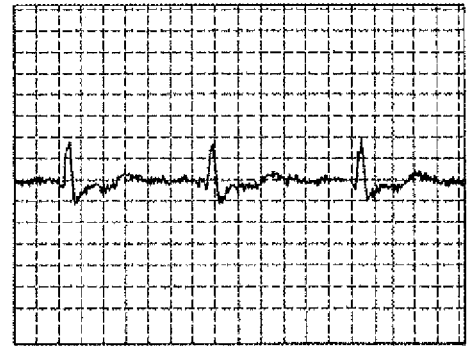
Figure 13D:
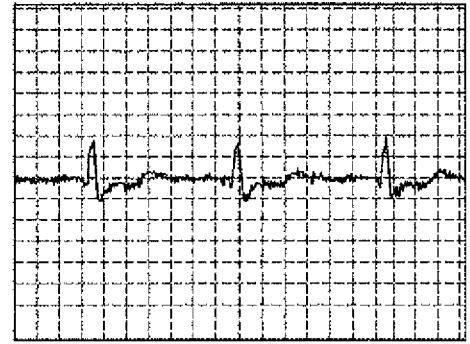

More specifically, FIG. 13A shows an output signal of a differential amplifying unit 1120 when a patch is attached in an arbitrary position. FIG. 13B shows an output signal of a differential amplifying unit 1120 when the patch of FIG. 13A is rotated by 90°. FIG. 13C shows an output signal of a differential amplifying unit 1120 when the patch of FIG. 13A is rotated by 180°. FIG. 13D shows an output signal of a differential amplifying unit 1120 when the patch of FIG. 13A is rotated by 270°. As recognized from FIGS. 13A-13D, nearly the same ECG signals can be obtained regardless of the attachment location of the multi-electrode module or the arrangement direction of the electrodes.

As noted above, FIG. 14 is a schematic diagram illustrating leads I, II and III of the Eindhoven's triangle, according to an embodiment of the present invention.

The ECG measurement using three lead positions on a basis of the chest are performed in the left-to-right or right-to-left direction for the lead I, from the upper right chest to the left to the abdomen for the lead II, and from the upper left chest to the left to the abdomen for the lead III, thereby making up the Eindhoven's triangle. Among the leads I, II and III, the R-peak of the lead II is largest because the direction of the lead II is nearly parallel to a heart axis, and the R-peak of the lead I is smallest because the direction of the lead I is nearly perpendicular to a heart axis, the basis of movement of the heart. As known, the R-peak is the peak of the R wave, and associated with the contractions of the ventricle and the atrium in synchronization with the heart beat.

Figure 15:
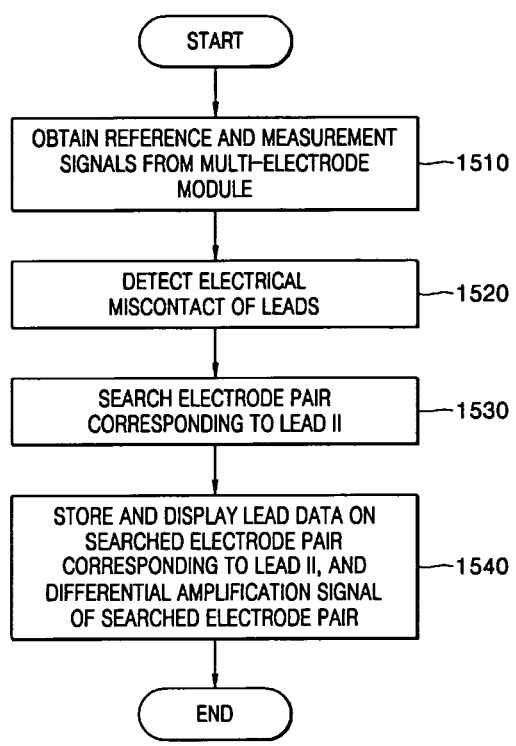
FIG. 15 illustrates a flow chart for a lead search method using a multi-electrode module, according to an embodiment of the present invention.

FIG. 15 illustrates a flow chart for a lead search method using a multi-electrode module, according to an embodiment of the present invention. The lead search can be performed in the microcontrollers 560 and 860 of FIGS. 5 and 8, for example.

In operation 1510, a plurality of reference signals and measurement signals are obtained by combining a plurality of electrodes of the multi-electrode module attached to the human skin. In this case, the electrode arrangement of FIG. 1 or 2 may be used as the multi-electrode module.

In operation 1520, electrical miscontact of the leads is detected by using the reference signals and the measurement signals, obtained in operation 1510.

In operation 1530, if the leads are at a normal state, as a result of operation 1520, an electrode pair corresponding to the lead II can be searched by using a plurality of differential amplification signals for the reference and measurement signals obtained in operation 1510.

In operation 1540, lead data on the found electrode pair corresponding to the lead II, and the differential amplification signal on the found electrode pair corresponding to the lead II are stored in the storage unit 580 and 880 and displayed on the display unit 570 and 870.

Figure 16:
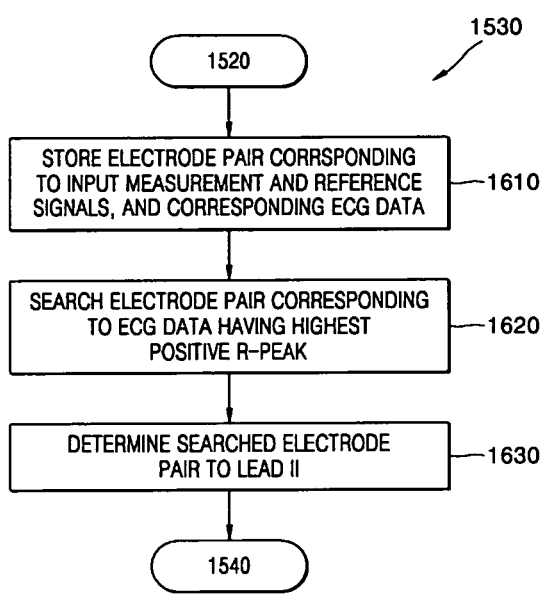
FIG. 16 illustrates a flow chart for a lead search operation of FIG. 15, according to an embodiment of the present invention.

FIG. 16 illustrates a flow chart for the lead search operation 1530 of FIG. 15 in detail.

In operation 1610, the electrode pair corresponding to the input measurement and reference signals, and corresponding ECG data are stored for every measurement and reference signal.

In operation 1620, the R-peaks of a plurality of ECG data stored in operation 1610 are compared to search an electrode pair corresponding to ECG data having a highest positive R-peak.

In operation 1630, it is determined that the electrode pair found in operation 1620 corresponds to the lead II.

Figure 17:
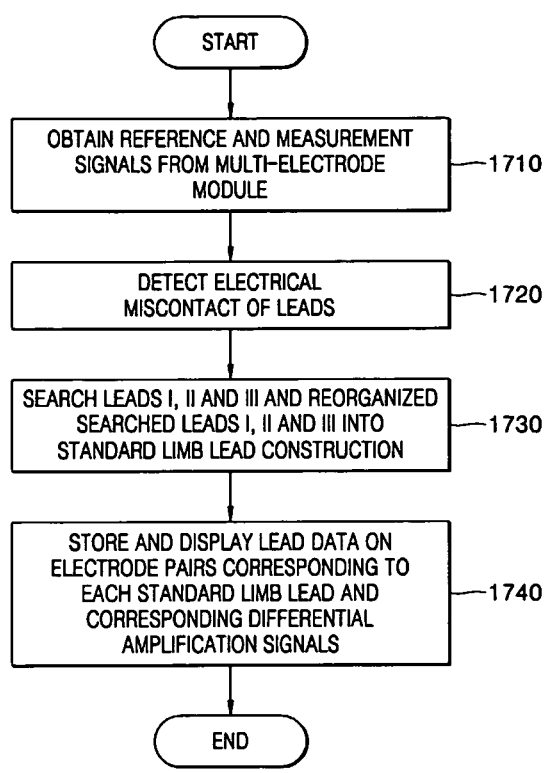
FIG. 17 illustrates a flow chart for a lead search method using a multi-electrode module, according to another embodiment of the present invention.

FIG. 17 illustrates a flow chart for a lead search method using a multi-electrode module, according to another embodiment of the present invention. Preferably, the lead search method of FIG. 17 is performed in the microcontroller 560 or 860 of FIG. 5 or 8, for example.

In operation 1710, a plurality of reference and measurement signals are obtained by combining a plurality of electrodes of the multi-electrode module attached to the human skin. In this case, the electrode arrangement of FIG. 1 or 2 may be utilized as the multi-electrode module.

In operation 1720, electrical miscontact of the leads is detected by using the reference and measurement signals obtained in operation 1710.

In operation 1730, if the leads are at a normal state, as a result of operation 1720, electrode pairs corresponding to the leads I, II and III can be searched for by using a plurality of differential amplification signals for the reference and measurement signals obtained in operation 1710. The found leads I, II and III can then be reorganized into a standard limb lead construction.

In operation 1740, lead data on the electrode pairs corresponding to each standard limb lead and corresponding differential amplification signals are stored in the storage unit 580 and 880 and displayed on the display unit 570 and 870.

Figure 18:
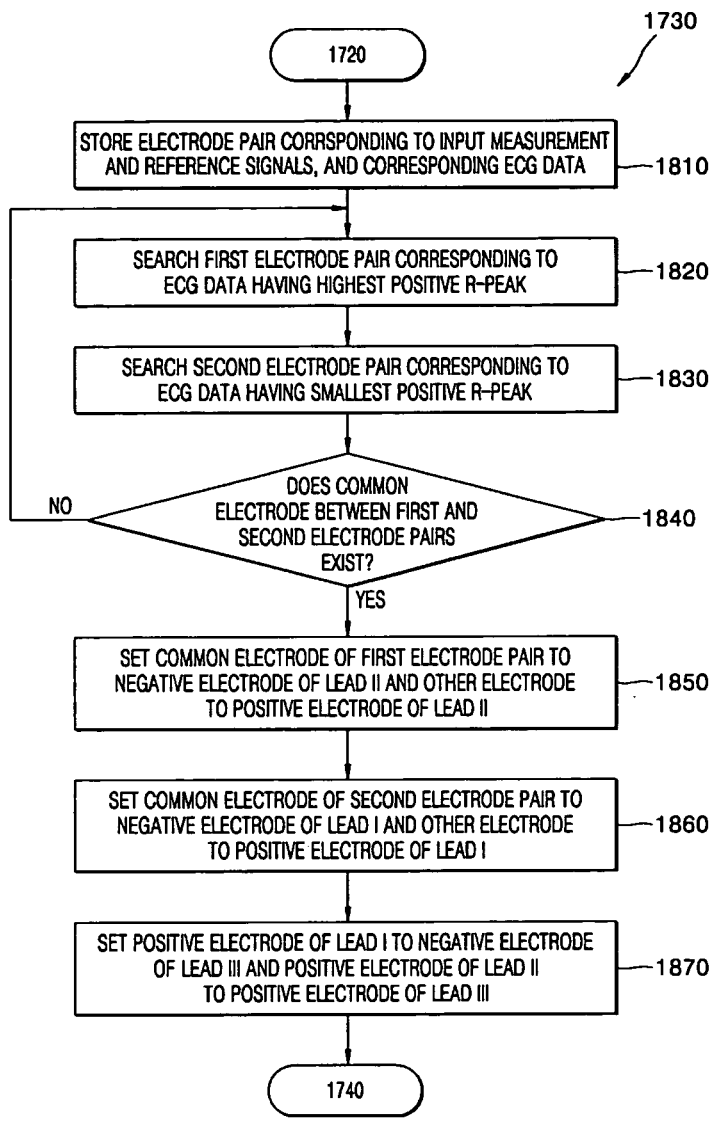
FIG. 18 illustrates a flow chart for reorganizing a standard limb lead of FIG. 17, according to an embodiment of the present invention.

FIG. 18 illustrates a flow chart for operation 1730 of reorganizing a standard limb lead arrangement of FIG. 17 in detail.

In operation 1810, information on the electrode pair corresponding to the input measurement and reference signals and corresponding ECG data are stored for every measurement and reference signal. If the multi-electrode module of FIG. 1 is adopted, one reference electrode and one measurement electrode may make up a single electrode pair. On the other hand, if the multi-electrode module of FIG. 2 is adopted, for example, one reference electrode and each measurement electrode may make up a plurality of electrode pairs.

In operation 1820, the R-peaks of a plurality of ECG data stored in operation 1810 are compared to search for a first electrode pair corresponding to ECG data having a highest positive R-peak.

In operation 1830, the R-peaks of a plurality of ECG data stored in operation 1810 are compared to search for a second electrode pair corresponding to ECG data having a smallest positive R-peak.

In operation 1840, it can be determined which electrode is common between the first electrode pair found in operation 1820 and the second electrode pair found in operation 1830. Preferably, the second electrode pair corresponding to the ECG data having the lowest R-peak is used as a basis of the common electrode examination of operation 1840. If there is no common electrode as a result of operation 1840, operation 1820 is repeated.

In operation 1850, if there is a common electrode, as a result of operation 1840, the first electrode pair found in operation 1820 can be determined to be a lead II. In this case, the common electrode is set as a negative electrode and the other electrode is set as a positive electrode.

In operation 1860, the second electrode pair found in operation 1830 can be determined to be the lead I. In this case, the common electrode is set as a negative electrode and the other electrode is set as a positive electrode.

Meanwhile, if there are at least two first electrode pairs corresponding to the ECG data having the highest R-peak based on the second electrode pair corresponding to the ECG data having the lowest R-peak, the nearest one to the positive electrode of the lead I is set as a positive electrode of the lead II.

In operation 1870, the positive electrode of the lead I, determined in operation 1860, is set as a negative electrode of the lead II, and the positive electrode of the lead II, determined in operation 1850, is set as a positive electrode of the lead III.

Now, the electrode pairs of the leads I, II and III will be described with reference to FIGS. 7A through 7F. The lead I has an electrode pair including the reference electrode 121 and the first individual electrode 123 to generate the waveform of FIG. 7A. In this case, the reference electrode 121 functions as a negative electrode of the lead I, and the first individual electrode 123 functions as a positive electrode of the lead I. The lead II has an electrode pair including the reference electrode 121 and the sixth individual electrode 128 to generate the waveform of FIG. 7F. In this case, the reference electrode 121 functions as a negative electrode of the lead II, and the sixth individual electrode 128 functions as a positive electrode of the lead II. Also, the lead III has an electrode pair including the first individual electrode 123 corresponding to the positive electrode of the lead I and the sixth individual electrode 128 corresponding to the positive electrode of the lead II. In this case, the first individual electrode functions as a negative electrode, and the sixth individual electrode 128 functions as a positive electrode.

The aforementioned apparatus embodiments shown in FIGS. 5, 8 and 11 have been separately described. However, most elements may be similar except the arrangement of the electrodes. Therefore, the aforementioned apparatus embodiments for measuring biological signals can be integrated into one apparatus for measuring biological signals, e.g., as shown in FIG. 19.

Figure 19:
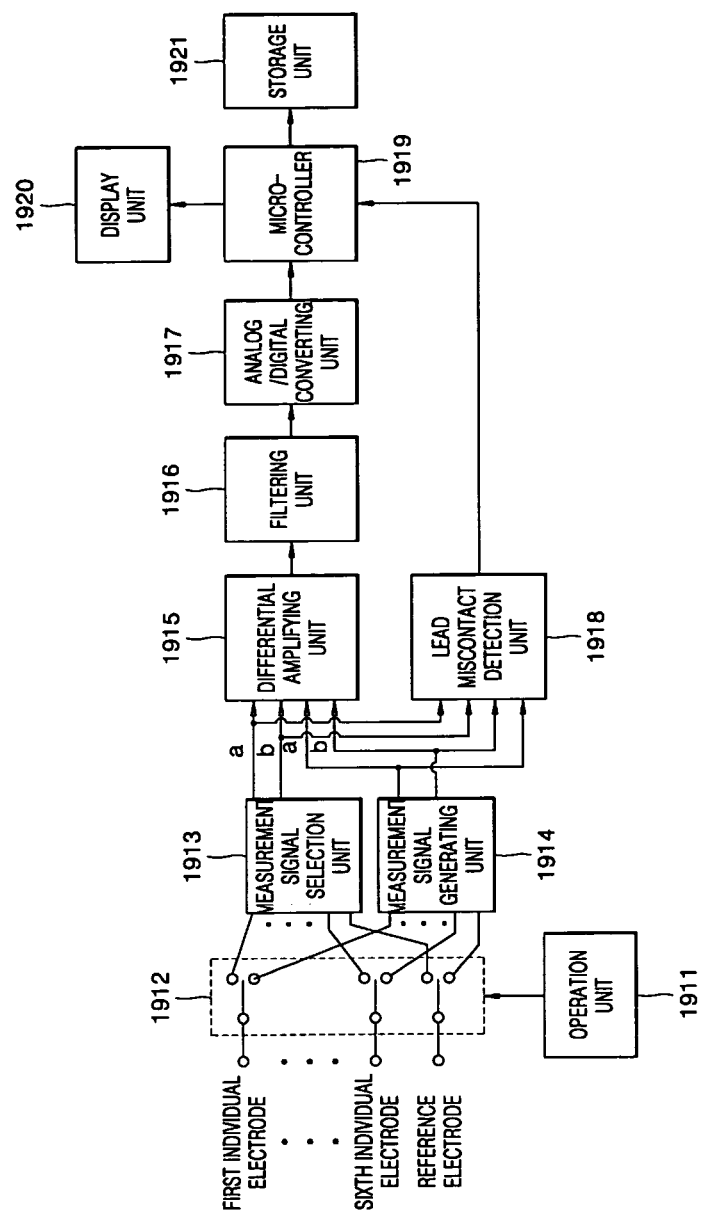
FIG. 19 illustrates a block diagram of an apparatus for measuring biological signals by using a multi-electrode module, according to still another embodiment of the present invention.

Referring to FIG. 19, an apparatus for measuring biological signals, according to another embodiment of the present invention includes an operation unit 1911, a switch unit 1912, a measurement signal selection unit 1913, a measurement signal generating unit 1914, a differential amplifying unit 1915, a filtering unit 1916, an A/D converting unit 1917, a lead miscontact detection unit 1918, a microcontroller 1919, a display unit 1920, and a storage unit 1921. The operation unit 1911, the switch unit 1912, the measurement signal selection unit 1913, and the measurement signal generating unit 1914 make up an electrode selection section. In addition, the differential amplifier unit 1915, the filtering unit 1916, the A/D converter unit 1917, the lead miscontact detection unit 1918, the microcontroller 1919, the display unit 1920, and the storage unit 1921 make up a signal processing section. Herein, the signal processing section may be similar to those shown in FIGS. 5, 8 and 11. The measurement signal selection unit 1913 may be similar to reference numeral 510 of FIG. 5. The measurement signal generating unit 1914 may be similar to reference numeral 1110 of FIG. 11. Also, the reference/measurement selection unit 810 shown in FIG. 8 may be applied instead of the measurement signal selection unit 1913.

The operation unit 1911 can be used to select a type of biological signal to be measured, e.g., by way of a user's operation, and generates a control signal for the switch unit 1912 depending on the selected biological signal. As another embodiment, the operation unit 1911 may be connected to the microcontroller 1919 to generate the control signal from the microcontroller 1919.

The switch unit 1912 has a plurality of switches corresponding to the first through sixth individual electrodes and the reference electrode. Depending on the control signal from the operation unit 1911 or the microcontroller 1919, the first through sixth individual electrodes and the reference electrode are connected to one of the measurement signal selection unit 1913 or the measurement signal generating unit 1914.

Embodiments of the present invention can also be embodied as computer readable code on a medium, e.g., a computer readable recording medium. The medium may be any data storage device that can store/transfer data that can thereafter be read by a computer system. Examples of media include read-only memory (ROM), random-access memory (RAM), CD-ROMs, magnetic tapes, floppy disks, optical data storage devices, and carrier waves (such as data transmission through the Internet). The media may also be a distributed network, so that the computer readable code is stored/transferred and executed in a distributed fashion. Also, functional programs, codes, and code segments for accomplishing embodiments of the present invention can be easily construed by programmers skilled in the art to which the present invention pertains.

According to embodiments of the present invention, it is possible to effectively search at least one lead for acquiring ECG data regardless of the polarity or arrangement of the electrodes of the biological signal electrode module. Therefore, even an inexperienced person can easily attach/remove the biological signal electrode module. Thus, it is possible to improve user's convenience.

By changing the connection of the electrodes of the biological signal electrode module, stable biological signals such as an ECG or a heart rate can be selectively acquired regardless of the arrangement of the electrodes.

Furthermore, since the leads are searched by analyzing the signals from each electrode, the obtained biological signals are adaptive to anatomical landmarks or different locations of the heart of each person. Therefore, it is possible to provide a more accurate diagnosis.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus for measuring biological signals, comprising:
   a multi-electrode module comprising a non-conductive patch and a sensor array including a ground electrode and a plurality of individual electrodes;
   an electrode selection unit to select a plurality of electrode pairs, including a reference electrode and a measurement electrode, from the plurality of individual electrodes based on a type of biological signal measured; and
   a signal processing unit to obtain the biological signals from the plurality of electrode pairs,
   wherein the signal processing unit obtains respective biological signals concurrently based on the selected plurality of individual electrodes, with the ground electrode, and each of the selected plurality of individual electrodes being different electrodes and the ground electrode being monitored during the measuring of the heart rate and measurement for the electrocardiograph analysis,
   wherein the electrode selection unit comprises:
   an operation unit to generate a predetermined control signal based on the type of the biological signal measured based on a user's input;
   a measurement signal selection unit to select an individual electrode placed at a center of the plurality of individual electrodes, disposed in a substantially circular arc, as the reference electrode for a reference signal, and sequentially selecting from the plurality of individual electrodes as the measurement electrode for a measurement signal based on the individual electrode selected to be the reference electrode;
   a measurement signal generating unit to select the individual electrode as the reference electrode for the reference signal and selecting the plurality of individual electrodes disposed on the substantially circular arc as the measurement electrode for the measurement signal; and
   a switch unit, in response to the control signal, to selectively connect the multi-electrode module to the measurement signal selection unit or the measurement signal generating unit.

2. An apparatus for measuring biological signals, comprising:
   a multi-electrode module comprising a non-conductive patch and a sensor array including a ground electrode and a plurality of individual electrodes;
   an electrode selection unit to select a plurality of electrode pairs, including a reference electrode and a measurement electrode, from the plurality of individual electrodes based on a type of biological signal measured; and
   a signal processing unit to obtain the biological signals from the plurality of electrode pairs,
   wherein the signal processing unit obtains respective biological signals concurrently based on the selected plurality of individual electrodes, with the ground electrode, and each of the selected plurality of individual electrodes being different electrodes and the ground electrode being monitored during the measuring of the heart rate and measurement for the electrocardiograph analysis,
   wherein the electrode selection unit comprises:
   an operation unit to generate a predetermined control signal based on the type of the biological signal measured based on a user's input;
   a reference/measurement signal selection unit to sequentially select each of the plurality of individual electrodes, disposed in a substantially circular arc, as the reference electrode for a reference signal, and selecting at least one of remaining plurality of individual electrodes disposed in the substantially circular arc as the measurement electrode, to measure a measurement signal based concurrently on the selected measurement electrode and the selected reference electrode;
   a measurement signal generating unit to select an individual electrode, as a center electrode, placed at a center of the plurality of individual electrodes disposed in the substantially circular arc as the reference electrode for the reference signal and shorting output signals of the plurality of individual electrodes disposed in the substantially circular arc, to measure a single measurement signal based concurrently on the shorted plurality of individual electrodes and the selected center electrode; and
   a switch unit, in response to the control signal, to selectively connect the multi-electrode module to the reference/measurement signal selection unit or the measurement signal generating unit.

3. The apparatus of claim 2, wherein the reference/measurement signal selection unit adds or shorts output signals of the remaining individual electrodes to provide the measurement signal.

* * * * *